US00PP17704P2

(12) United States Plant Patent
Olesen et al.

(10) Patent No.: US PP17,704 P2
(45) Date of Patent: May 8, 2007

(54) ***CLEMATIS* PLANT NAMED 'EVIPO009'**

(50) Latin Name: *Clematis viticella*
Varietal Denomination: EVIpo009

(75) Inventors: Mogens N. Olesen, Fredensborg (DK); Raymond J. Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 512 days.

(21) Appl. No.: 10/719,754

(22) Filed: Nov. 21, 2003

(51) Int. Cl.
*A01H 5/00* (2006.01)

(52) U.S. Cl. ..... Plt./228

(58) Field of Classification Search ..... Plt./228
See application file for complete search history.

*Primary Examiner*—Kent Bell

(57) ABSTRACT

A new *Clematis* cultivar which is well suited to propagation is glasshouses. With a tall growth habit, profuse, white flowers, and continuous summer flowering. The variety successfully propagates from softwood cuttings and is suitable for cultivation in commercial glasshouses. This new and distinct variety has shown to be uniform and stable in the resulting generations from asexual propagation.

1 Drawing Sheet

SUMMARY OF THE INVENTION

Botanical classification: *Clematis 1* Genus—*Clematis*. Species—*viticella*.

Variety denomination: 'EVIpo009'.

Commercial classification: Early, large-flowering cultivar.

The present invention constitutes a new and distinct variety of *Clematis* which originated from a chance pollination between the female seed parent an unnamed, non-patented plant and an unknown male pollen parent plant.

'Evipo009' may be distinguished from its female seed parent primarily by flower color.

The objective of the selection of this *Clematis* variety for commercial glasshouse and nursery culture was to create a new and distinct variety with unique qualities that this variety has:

1. Large white flowers;
2. Compact growth;
3. Red/Brown flower center.

These qualities required improvement in *Clematis* varieties that were in commercial cultivation and the objectives have been substantially achieved in the new variety, as evidenced by the unique combination of characteristics that are present in 'EVIpo009' which distinguish it from all other varieties of which we are aware.

The seeds from the aforementioned chance pollination were germinated and evaluations of the resulting seedling plants were conducted in a controlled environment. As a result, 'EVIpo009' was selected by Raymond J. Evison and Mogens N. Olesen in their *Clematis* development program in Domarie Vineries Les Sauvagees, St. Sampsons, Guernsey, Channel Islands, United Kingdom in April 1997.

Asexual reproduction of 'EVIpo009' by cuttings was first done by Raymond J. Evison and Mogens N. Olesen in Domarie Vineries Les Sauvagees, St. Sampsons, Guernsey, Channel Islands, United Kingdom in June 1997. This initial and subsequent propagations have demonstrated that the characteristics of 'EVIpo009' are true to type and are transmitted from one generation to the next.

BRIEF DESCRIPTION OF THE DRAWING

The accompanying color illustration show as true as is reasonably possible to obtain in color photographs of this type:

FIG. 1.1 Stem with new growth and mature leaves, showing the attachment of petioles;

FIG. 1.2 Mature compound leaf;

FIG. 1.3 Flower buds closed;

FIG. 1.4 Open Flower, lower part, and tepals, detached;

FIG. 1.5 Open flower viewed from the side and above.

DETAILED DESCRIPTION OF THE VARIETY

The following is a detailed description of 'EVIpo009', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing *Clematis* variety is 'EVIrin', a patented variety described and illustrated in U.S. Plant Pat. No. 12,838 issued on Aug. 13, 2002. Chart 1 details several physical characteristics 'EVIpo009' and the comparison variety.

CHART 1

| | 'EVIpo009' | 'EVIrin' |
|---|---|---|
| Flower main color | White Group N155A. | Violet Group 84D. |
| Undulation of tepal margin | Slight | Medium-strong |
| Anther color | Red-Purple Group 59B | Dark red |

FLOWER AND FLOWER BUD

Blooming habit: Continuous. Flowering from May through September.

Flower bud:

*Size.*—40 to 50 mm in length. Bud diameter is 12 to 15 mm.

*Bud form.*—Long ovoid.

*Bud color.*—Yellow-Green Group 144A at ¼ opening.

Peduncle:

*Surface.*—Smooth.

*Length.*—90 to 120 mm average length.

*Color.*—Yellow-Green Group 144B.

*Strength.*—Erect.

Receptacle: None.

*Borne.*—Normally singularly, some later season will be Borne on Compound Cymes.

Flower bloom:

*Size.*—140 to 180 mm in diameter.

*Form.*—Upon opening, flat, with tepals held straight. Depth: Little depth 5 to 10 mm but anthers and stigma protrude giving the flower a total depth of 15 to 20 mm.

*Fragrance.*—None to very light.

*Lasting quality on plant.*—7 to 12 days.

*Lasting quality as a cut flower.*—2 to 5 days.

Tepals:

*Tepal color.*—Upon opening, White Group 155A on both upper and lower surfaces. After opening, White Group 155A on both upper and lower surfaces.

*Variations.*—When young the longitudinal region of the tepal undersurface may show a slight Yellow-Green Group 144A coloration. Occasionally flowers may show a slight pink coloration of Purple Group 65A.

*Quantity.*—Single.

*Shape.*—Elliptical.

*Cross section.*—Normally straight, occasionally slightly cupped.

*Undulation of margin.*—Entire with slight undulations.

*Tepal apex.*—Cuspidate.

*Recurvature of tip.*—None.

*Persistence.*—Drop off cleanly.

*Arrangement.*—Tepals are arranged regularly.

Reproduction organs:

*Pollen.*—Quantity: Average. Color: Yellow-White Group 158C.

*Anthers.*—Size: Large. Color: Red-Purple Group 59B. Arrangement: Regular.

*Filaments.*—Color: White Group N155A.

*Stigmas.*—Protrude from anthers as flower ages.

*Styles.*—Color: White Group 155A.

*Pistils.*—Quantity: 40 to 60.

PLANT

Plant form: Climbing and spreading depending on host.

Plant growth: Moderately vigorous.

Height: Seasons growth attains 2.0 to 2.5 meters.

Spread: Seasons growth is normally 1.5 to 2 meters.

Hardiness: Trials to date show the variety hardy in USDA Zones 4–9.

Stems:

*Color.*—Young wood: Red-Purple Group 61A. Older wood: Greyed-Orange Group 165C.

*Internodes.*—Shape: Cylindrical. Length: 80 to 120 mm.

*Bark.*—Young wood: Smooth. Older wood: Smooth.

Plant foliage: Deciduous. Trifoliate with three broad elliptical to ovate leaflets.

*Terminal leaflet size.*—40 to 50 mm wide×70 to 90 mm in length.

*Abundance.*—Above average.

*Color.*—New growth: Upper and lower surfaces are Green Group 137B. Older growth: Upper surface is Green Group 137A. Lower Surface is Green Group 137B.

Plant leaves and leaflets:

*Stipules.*—Absent.

*Petioles.*—Size: Average length: 60 to 80 mm. Color: Green Group 143A maturing to Red-Purple Group 61A.

*Petioloule.*—Length: 10 to 30 mm. Color: Green Group 143A maturing to Red-Purple Group 61A.

*Leaf edge.*—Terminal leaflet margin is entire with mild undulations.

*Leaflet shape.*—Base: Acute to rounded. Apex: Acute.

*Texture.*—Medium texture.

*Surface.*—Upper side: Rough. Lower side: Rough.

*Glossiness.*—Matte Finish.

Disease resistance: Subject to any disease that normally attacks the species.

It is claimed:

1. We claim a new and distinct variety of *clematis* plant, as herein shown and described, due to its abundant white flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

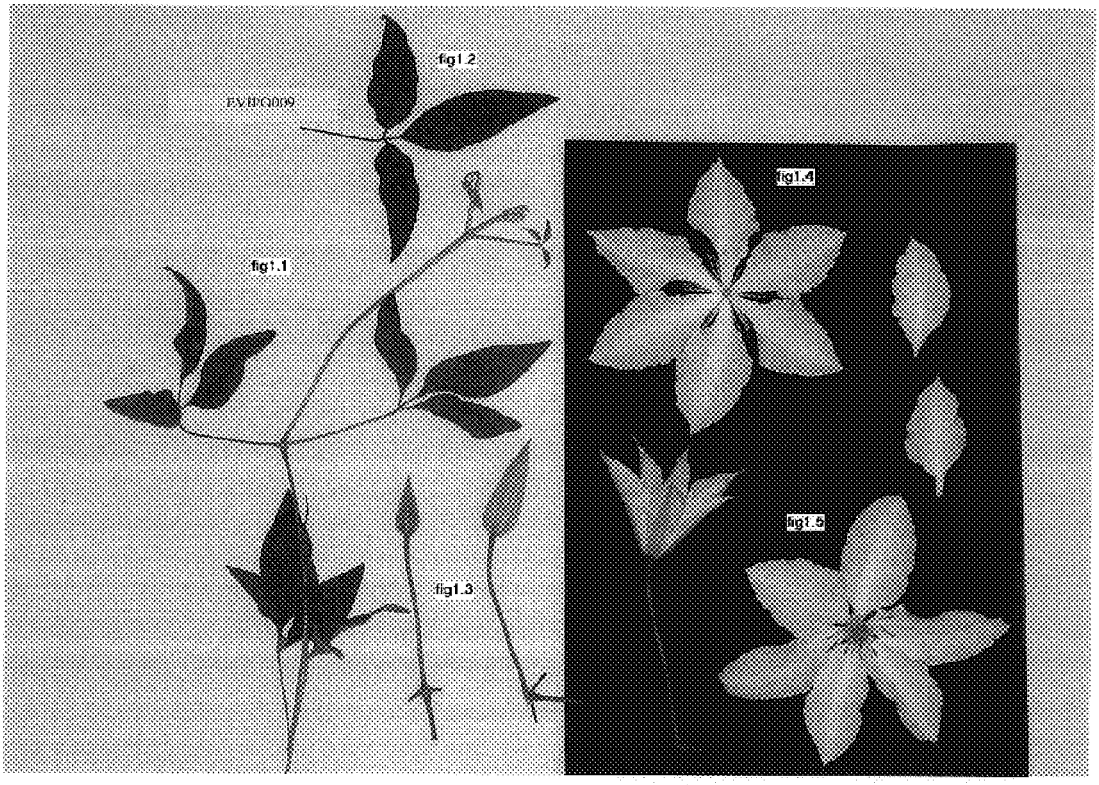
fig1.2
fig1.1
fig1.4
fig1.5
fig1.3